US009687841B2

(12) United States Patent
Hofmann

(10) Patent No.: US 9,687,841 B2
(45) Date of Patent: Jun. 27, 2017

(54) NEEDLE GUIDE WITH CENTERING FOR SEPTUM PIERCING

(71) Applicant: Bruker BioSpin GmbH, Rheinstetten (DE)

(72) Inventor: Martin Hofmann, Bad Herrenalb (DE)

(73) Assignee: Bruker BioSpin GmbH, Rheinstetten (DE)

(*) Notice: Subject to any disclaimer, the term of this patent is extended or adjusted under 35 U.S.C. 154(b) by 0 days.

(21) Appl. No.: 15/336,257

(22) Filed: Oct. 27, 2016

(65) Prior Publication Data

US 2017/0120234 A1    May 4, 2017

(30) Foreign Application Priority Data

Oct. 28, 2015    (DE) ........................ 10 2015 221 024

(51) Int. Cl.
*B01L 3/00*    (2006.01)
*G01N 1/00*    (2006.01)
(Continued)

(52) U.S. Cl.
CPC ............. *B01L 3/021* (2013.01); *B01L 3/0289* (2013.01); *B01L 3/0293* (2013.01);
(Continued)

(58) Field of Classification Search
CPC ...... B01L 3/021; B01L 3/0289; B01L 3/0296; B01L 2300/0672; G01N 35/1002; G01N 35/1079; G01N 2035/0403
See application file for complete search history.

(56) References Cited

U.S. PATENT DOCUMENTS 3,981,200 A    9/1976    George et al.
3,991,627 A    11/1976    Laird et al.
(Continued)

FOREIGN PATENT DOCUMENTS

DE    2537606 A1    4/1976
DE    3884280 T2    1/1994
(Continued)

OTHER PUBLICATIONS

Office Action in corresponding German Application No. 102015221024.3, dated Jul. 27, 2016, along with a partial English translation.
(Continued)

*Primary Examiner* — Jennifer Wecker
(74) *Attorney, Agent, or Firm* — Edell, Shapiro & Finnan, LLC

(57) ABSTRACT

A pipetting device (2) for removing fluid from a sample vessel (52) includes a pipetting needle (4) and an auxiliary cannula (18) for piercing a septum, designed to guide the pipetting needle axially through the auxiliary cannula. The pipetting device has a guide arm (6), on the lower end (10) of which is arranged an end plate (12) that is axially displaceable along the guide arm against a resilient resistance. A centering device (14) inserts into the end plate of the guide arm, and at least three centering fingers (26) with conical bevels (34) are constructed on the radial outside of the centering device, distributed around the circumference thereof, and forming a holding-down device for the sample vessel. The disclosed construction makes possible to reliably pierce the septum of a sample vessel and to easily pull the pipetting needle out of the septum again even with thin pipetting needles.

15 Claims, 11 Drawing Sheets

(51) Int. Cl.
  *B01L 3/02*  (2006.01)
  *B67C 9/00*  (2006.01)
  *G01R 33/30*  (2006.01)
  *G01N 35/10*  (2006.01)
  *G01N 35/04*  (2006.01)

(52) U.S. Cl.
  CPC ....... *B01L 3/0296* (2013.01); *B01L 2200/025* (2013.01); *B01L 2300/0672* (2013.01); *G01N 35/1002* (2013.01); *G01N 35/1079* (2013.01); *G01N 2035/0403* (2013.01); *G01R 33/302* (2013.01)

(56) References Cited

U.S. PATENT DOCUMENTS

| | | | |
|---|---|---|---|
| 4,861,553 A * | 8/1989 | Mawhirt | G01N 35/021 198/802 |
| 5,240,679 A | 8/1993 | Stettler | |
| 5,517,867 A | 5/1996 | Ely et al. | |
| 5,756,905 A | 5/1998 | Ueda | |
| 6,666,100 B1 | 12/2003 | Snyder | |
| 6,973,846 B2 | 12/2005 | Bremer et al. | |
| 2002/0196023 A1* | 12/2002 | Hofmann | G01R 33/30 324/321 |
| 2004/0241864 A1* | 12/2004 | Sattler | B01L 3/50825 436/43 |
| 2009/0246085 A1 | 10/2009 | Watson et al. | |

FOREIGN PATENT DOCUMENTS

| | | |
|---|---|---|
| DE | 10219790 C1 | 10/2003 |
| EP | 0478905 A1 | 4/1992 |

OTHER PUBLICATIONS

Spark Holland BV., "Triathlon user manual", Pieter de Keyserstraat 8, NL-7825 VE Emmen, Netherlands, Apr. 2000.

Bruker Biospin GMBH, "SamplePro Tube: Customer Information", Silberstreifen 4, Germany, Apr. 2015.

European Search Report in counterpart European Application No. EP16194424, mailed Mar. 1, 2017, 3 pages, with English translation, 1 page.

\* cited by examiner

NEEDLE GUIDE WITH CENTERING FOR SEPTUM PIERCING

CROSS REFERENCE TO RELATED APPLICATIONS

This application claims foreign priority under 35 U.S.C. §119(a)-(d) to German Application No. 10 2015 221 024.3 filed on Oct. 28, 2015, the entire contents of which are hereby incorporated by reference.

FIELD OF THE INVENTION

The invention relates to a pipetting device for sampling fluid from a sample vessel that is sealed on the top side with a septum, comprising a pipetting needle as well as an auxiliary cannula for piercing the septum, designed to guide the pipetting needle axially through the auxiliary cannula.

Such a pipetting device became known, for instance, from the "Triathlon user manual" published by Spark Holland B. V., Pieter de Keyserstraat 8, NL-7825 VE Emmen, the Netherlands, from April 2000.

BACKGROUND

The present invention relates generally to the area of the preparation of liquid samples in a sample vessel, particularly to the sampling fluid from a sample vessel or the filling of sample fluid into a sample vessel, wherein the sample vessel is sealed on the top side with a septum. The invention relates particularly to the preparation of samples to be analyzed using NMR spectroscopy. However, the applicability of the invention is not limited to this area.

NMR spectroscopy is a widely used method of measurement with which chemical compounds can be analyzed. In NMR spectroscopy, a sample to be measured, situated in a test tube, is typically placed into a probehead and measured in the NMR spectrometer.

A so-called XYZ liquid handler is typically used to prepare samples for NMR measurements. Such liquid handlers comprise a pipetting device that can be moved in three spatial directions (X, Y, Z). A plurality of samples to be studied are prepared in sample vessels, each of which is sealed with a septum. These septa must be pierced by a needle with a bevel in order to reach the sample. The XYZ liquid handler usually has a so-called septum piercing needle for this purpose. The septum piercing needle is typically used both for piercing the septum and for handling the sample fluid.

A liquid handler in which freely hanging septum piercing needles are used became known from the company brochure "SamplePro Tube—Customer Information" published by Bruker BioSpin GmbH, Silberstreifen 4, D-76287 Rheinstetten and dated 27 April 2015. This liquid handler further comprises a holding-down device for sample vessels.

This liquid handler enables simple monitoring of the sample position with the aid of the holding-down device through simultaneous measurement of a motor current during movement to a set Z-position (vertical position) for some but not all commonly used sample vessels. Particularly with densely arranged vessels with a small opening, it is not possible to check the sample position.

Besides sample vessels, which can sometimes have a relatively large top-side opening (3 to 5 mm diameter), objects with very small inside diameters (such as NMR tubes, for example), among other things, must also be filled. There are NMR tubes that must be filled with prepared sample fluid which have a 1.0 mm or 1.7 mm outside diameter and correspondingly small inside diameter of only 0.7 mm or 0.8 mm or 1.4 mm. Such NMR tubes can only be approached with a thin needle with small outside dimensions. However, needles with outside diameters of less than 1 mm are too labile to pierce septa, which are up to 3 mm thick.

Septum piercing needles can have a length of up to 200 mm with outside diameters between 0.5 mm and 1.5 mm. They are therefore relatively labile. It is then necessary to guide the needles in order to prevent buckling or bending of the needles.

In the "Triathlon user manual" cited at the outset, a pipetting device for a liquid handler is described that has a piercing needle and a sample needle. The piercing needle is used to pierce a septum sealing a sample vessel. The analysis needle is arranged concentrically within the piercing needle and is used to handle sample fluids.

Due to its construction and mechanism for moving the pipetting device, however, a liquid handler is prone to certain imprecisions in the spatial alignment of the pipetting device. Furthermore, the sample vessels used have (dimensional) tolerances. The positioning of the sample vessels in a holding device is also subject to certain (positional) imprecisions. This can result in deviations in the relative position between the pipetting device and the sample vessels, quite possibly on the order of +/−1 mm. Moreover, there are sample vessels with very narrow openings in NMR applications, such as so-called NMR SampleJet tubes, for example, which have an opening diameter of approximately 2 mm. The danger therefore exists of the needles used in the pipetting device of the liquid handler are not striking the center of the septum or even hitting an upper edge of the sample vessel. Such out-of-position of the needles must be avoided, since it would inevitably result in the destruction of the needles.

Furthermore, the friction of the septum retains a needle that is inserted into the septum. When the needle is pulled out, the septum, or a sample vessel comprising the septum, must therefore be actively pushed off. This can be accomplished by anchoring the sample vessel firmly on a work plate, although that requires an individualized and often elaborate mechanism for each position and vessel shape.

SUMMARY

It is an object of the invention to provide a structurally simple pipetting device that makes it possible even when using very thin pipetting needles to reliably pierce the septum of a sample vessel and to easily pull the pipetting needle out of the septum again.

This object is achieved by the present invention in a manner that is just as surprisingly simple as it is effective, namely in that the pipetting device comprises a guide arm on the lower end of which is arranged an end plate that is axially displaceable along the guide arm against a resilient resistance, in that a centering device is provided that can be inserted into the end plate of the guide arm, and in that at least three centering fingers with conical bevels are constructed on the radial outside of the centering device, distributed around the circumference thereof, forming a holding-down device for the sample vessel and able to engage around the top portion of the sample vessel from the outside during operation.

Through use of the centering device, the pipetting device can be aligned precisely relative to the sample vessel. In this way, it can be ensured that the septum is always pierced in its center. The septum can be made, for example, of silicone, rubber, PTFE, or of various combinations of materials, such as silicone with a PTFE coating, for example.

The auxiliary cannula is used to pierce the septum. For this purpose, it can be embodied so as to have an outside diameter that is large compared to the pipetting needle as well as a greater wall thickness. The auxiliary cannula also serves to guide and support the pipetting needle. The pipetting needle can be passed axially through the auxiliary cannula. An inside diameter of the auxiliary cannula therefore corresponds at least to an outside diameter of the pipetting needle.

The centering of the pipetting device on the sample vessel is necessary particularly if an opening of the sample vessel that is sealed by the septum has a small diameter. In such cases, even small positioning errors result in an upper edge of the sample vessel being struck upon attempting to pierce the septum. The centering of the pipetting device on other sample vessels with a larger septum opening, such as 2 ml auto-sampler vials, for example, is also advantageous. A septum is substantially easier to pierce in the center than outside of the center. The stress on the auxiliary cannula is therefore less.

The centering device can be inserted into the end plate of the guide arm. The end plate is arranged on the underside of the guide arm. The end plate is displaceable along the guide arm against a resilient resistance. The guide arm can be designed with a linear guide for the end plate for this purpose. The resilient resistance is preferably provided by a spring, particularly a cylindrical coil spring. Alternatively, a leaf spring, a gas spring, a rubber spring, or other mechanisms with elastically deformable elements can also be provided. The resilient resistance counteracts a movement of the end plate toward a top-side suspension of the guide arm. A home position into which the resilient resistance tries to push the end plate can be defined by a stop on the guide arm.

The centering device has at least three centering fingers with conical bevels that are distributed along the radial outside circumference of the centering device. The lock-in range of the centering device is enlarged by the bevels of the centering fingers. Sample vessels that are initially arranged significantly to the side of a center axis of the centering device are caught by the centering fingers and pressed into the center of the centering device upon lowering of the centering device. In this way, it can be achieved that objects (i.e., sample vessels in particular) with outside diameters of 6 to 14 mm, for example, can be reliably captured and centered. Depending on their outside diameter, the centered sample vessels can abut with a top-side edge against the bevels of the centering device, or be received within a substantially cylindrical or cylindrical segment-shaped centering recess.

During the operation of the pipetting device, the centering device is pressed by the resilient resistance against the sample vessel upon the lowering of the top-side suspension of the guide arm. In this way, it can be achieved that the sample vessel slides into the center of the centering device and that the sample vessel is held there securely. The centering fingers then engage around the sample vessel on the top side thereof from the outside.

The auxiliary cannula is typically fastened to the guide arm above the displaceable end plate. The auxiliary cannula can be screwed into a projection of the guide arm for this purpose. A longitudinal axis of the auxiliary cannula is usually oriented parallel to a direction of longitudinal extension of the guide arm.

Preferably, the auxiliary cannula is not displaceable in relation to the top-side suspension of the guide arm, particularly not in the axial direction—that is, along the guide arm. A lower, free end of the auxiliary cannula is designed to pierce the septum. If the end plate with the centering device is in a lower position, the free end of the auxiliary cannula is preferably arranged within the centering device. If the centering device is pushed upward against the resilient resistance, the free end of the auxiliary cannula then emerges from the centering device. The free end of the auxiliary cannula can then pierce the septum of the sample vessel. The centering function is maintained throughout the entire procedure, since the pipetting needle is displaced relative to the centering device, whereas the centering device is always pressed by the resilient resistance onto the sample vessel.

The pressing of the centering device against the sample vessel by the resilient resistance also has the effect that the sample vessel is not lifted when the auxiliary cannula is pulled out of the septum. The centering fingers that engage around and hold the top side of the sample vessel thus form a holding-down device for the sample vessel. In their capacity as seals, septa per se have a high level of friction, so the auxiliary cannula must be pulled out of them forcefully. Preferably, the resilient resistance is therefore set up and coordinated with the longitudinal position of the free end of the auxiliary cannula relative to the guide arm such that sufficient contact pressure of the centering device against the sample vessel still exists when the auxiliary cannula has already been pulled out of the septum to the greatest possible extent. The centering device on the resiliently supported end plate thus forms a general (universally usable) stripper that can be used in various types of sample vessel. Separate, elaborate devices for anchoring the sample vessels on a platform so that they cannot be lifted in the vertical direction are therefore not necessary when using the pipetting device according to the invention.

With the present invention, the following advantages are also particularly achieved:

Pipetting needles having different dimensions can be used, for example with a length between 100 mm and 250 mm, an outside diameter between 0.5 mm and 2.5 mm and/or an inside diameter between 0.25 mm and 1.6 mm. Depending on the application, it can be necessary to use pipetting needles having different outside diameters (0.5 mm to 2.5 mm) on the same system. The auxiliary cannula acts as a needle guide. Auxiliary cannulas can be given different inside diameters, each of which is only slightly larger than the outside diameter of the pipetting needle being used, whereby the pipetting needle is guided in a precise and reliable manner in the auxiliary cannula.

The use of pipetting needles with small outside diameters is made possible. Particularly, the pipetting needles need not have such a stable design that they are able to pierce the septum. The auxiliary cannula can be short and relatively strong (large diameter, large wall thickness) in order to enable even thick septa to be pierced. The auxiliary cannula creates an opening through which the pipetting needle can be inserted into and removed from the sample vessel effortlessly and without stressing the pipetting needle.

The centering device ensures central penetration of the septum, particularly even in the case of critical sample vessels with a small opening. Due to the conical bevels of the centering fingers in an area of contact with the sample vessel, the centering device has an overall conical shape, thereby creating a catch range that covers up to +/−3 mm depending on the radial positional deviations between sample vessel and centering device. That is, even a sample vessel that is initially arranged off-center relative to the centering device is caught by the centering device and aligned concentrically to the centering device when the centering device is pressed down on the same. The septum can then be pierced precisely in the center.

The resilient supporting of the centering device on the guide arm ensures that the sample vessel is held down when the auxiliary cannula is pulled out.

An embodiment of the monitoring cell according to the invention is especially preferred in which the centering device can be screwed into the end plate. This enables the centering device to be fastened easily and securely in the end plate. In particular, the centering device can also be replaced quickly. It can be necessary to change the centering device due to wear, or in order to adapt to the specific conditions of the application.

An alternative embodiment to this configures the centering device to be engaged, clamped or inserted into the end plate with a bayonet socket. This enables the centering device to be changed very easily. In particular, such fastening mechanisms can also be operated safely and reliably by laboratory staff.

An embodiment that is especially preferred is one in which an anti-twist device is provided that is embodied such that it enables a defined alignment of the centering device relative to the end plate, with the anti-rotation device having particularly at least two, preferably four, top-side projections of the centering device that engage laterally around the end plate. The anti-twist device ensures that the alignment of the centering device can no longer change during use. The precise alignment of the centering fingers is important in order to prevent conflicts with neighboring sample vessels. In particular, in the case of tightly arranged sample vessels, it is possible to utilize the clearances between the sample vessels to move the centering fingers past the sample vessels only if the centering device is oriented with precision. Typically, the sample vessels are arranged next to one another so as to be tightly packed in a quadratic pattern. Even a slight rotation of the centering device would negate the function, since the centering finger would collide with neighboring sample vessels. The projections arranged on the top side and a width of the end plate are coordinated with one another such that the centering aid adjusts itself automatically upon insertion and is secured in the correct alignment against rotation.

Another advantageous embodiment is one in which a provision is made that the centering device has on its bottom side a preferably annular lift-off aid arranged coaxially to the auxiliary cannula. With the lift-off aid, possible droplet formation on the auxiliary cannula can be prevented from causing sample vessels to become stuck on the centering device as a result of adhesion and removed from their original position. To wit, liquid droplets cannot be completely prevented from adhering to both the pipetting needle, the auxiliary cannula and the centering device after pipetting or after a cleaning and washing procedure. Without the lift-off aid on the bottom side of the centering device, the danger exists that the sample vessel will "stick" as a result of adhesive forces of the liquid between the septum and/or sample vessel and the centering aid and be removed from its position, or that the pipetting device will be damaged upon further spatial movement of the pipetting device. Through the lift-off aid, the contact surface of the centering device is reduced so much that this effect is prevented.

The lift-off aid can also particularly be formed by ring segments. The lift-off aid ensures that, after the auxiliary cannula is pulled out of the septum, the centering device detaches from the sample vessel and can be lifted off of the same. For this purpose, a contact surface between the septum and the centering device is reduced by the lift-off aid. The lift-off aid prevents large-surface contact of the centering device with the septum. Instead, one or more small areas of contact are created. Particularly, a very narrow (e.g., with a width of less than 1.0 mm or less than 0.6 mm), annular area of contact can be established. In this way, adhesive forces or the like between the centering device and the sample vessel and/or the septum can be reduced so much that the weight of the sample vessel is sufficient to overcome these forces.

One preferred embodiment is characterized in that a ventilation channel is established for the sample vessel between the auxiliary cannula and the pipetting needle when the pipetting needle passes axially through the auxiliary cannula. This enables the precise removal of a predetermined volume of sample fluid from the sample vessel or the precise filling of a predetermined volume of sample fluid into the sample vessel.

With the pumps usually used for pipetting, the conveyance (aspirate and dispense) of exact volumes is pressure-dependent. A pressure equalization between the surroundings and an interior space of the sample vessel is therefore necessary in order to precisely adhere to a desired quantity of liquid (volume of sample fluid to be aspirated or dispensed). After the septum is pierced, the sample vessel must therefore be ventilated in order to prevent under-pressure when the sample fluid is aspirated out of the sample vessel, or over-pressure during the dispensing of sample fluid into the sample vessel. To establish the ventilation channel, spacing is preferably set up between an outer wall of the pipetting needle and an inner wall of the auxiliary cannula. In particular, an outside diameter of the pipetting needle can be selected so as to be smaller than an inside diameter of the auxiliary cannula.

The pipetting needle can then be arranged concentrically or off-center in the auxiliary cannula. Alternatively or in addition, the outside of the pipetting needles and/or the inside of the auxiliary cannula can also be provided with a continuous notch in the longitudinal direction, such as in the manner of an engraving. In any case, a ventilation channel is opened for the sample vessel that enables a pressure equalization between the surroundings and the interior space of the sample vessel. In this way, it can be achieved that the same pressure conditions are always prevalent in the sample vessel during pipetting.

One advantageous embodiment makes a provision that the centering fingers of the centering device are beveled on the bottom side in the circumferential direction of the centering device. This enables conflicts with neighboring sample vessels to be minimized, i.e., the centering fingers can be prevented from colliding with directly adjacent sample vessels.

One embodiment is preferred in which the centering device has indentations in the shape of a circular segment (circular section) between the centering fingers. In this way, it can be achieved that only a small amount of space needs to be furnished between neighboring sample vessels (e.g., only 3 mm or even only 2 mm) in order to enable the centering device to engage around them. The centering fingers project into free spaces between mutually adjacent sample vessels, whereas the indentations are arranged between the neighboring sample vessels. This minimizes the space required between the sample vessels.

The sample vessel is typically arranged in a tightly packed manner with other sample vessels on a work platform. For example, 96 NMR tubes can be arranged next to one another very densely—that is, with only a small amount of spacing—in the well plate format. By virtue of the centering device with indentations, they can be approached with precision using the pipetting device. Another function of this centering device is making a determination of whether a selected sample vessel is located in an approached position or whether this position is unoccupied. To achieve this, the centering device must be able to travel lower than a centering position (at least lower than the vertical position of the centering device in which the centering device is seated so as to be centered on the sample vessel). To enable this lower position between the other vessel positions to be reached, the centering aid is also designed with indentations having the shape of a circular segment.

In one especially preferred embodiment, a provision is made that the centering fingers are arranged so as to be distributed uniformly around the periphery of the centering device. The sample vessels are typically arranged uniformly in holders. This results in uniformly distributed free spaces into which the centering device can engage with uniformly distributed fingers. Furthermore, this ensures that the centering device is supported on the sample vessel equally in all horizontal directions.

One embodiment that is very especially preferred is one in which the centering device has four centering fingers that are respectively arranged opposite one another in pairs. As a rule, the sample vessels are arranged uniformly in rows and lines in holders. This results in four free spaces on the sample vessel respectively arranged opposite one another in pairs. The centering device can engage into these free spaces if the centering fingers are respectively arranged opposite one another in pairs.

An embodiment is also advantageous in which the centering device can also be inserted into the end plate of the guide arm without a tool and removed from the end plate. This enables the especially fast and easy replacement of the centering device. Particularly, this makes it possible even for technically untrained laboratory staff or support personnel to safely and flawlessly exchanging the centering device. It can be necessary to replace the centering device if sample vessels with different outside diameters and/or other pipetting needles and/or other auxiliary cannulas are to be used.

The scope of the invention also encompasses a method for detecting the presence and, optionally, the position of a sample vessel using the pipetting device according to the invention described above. This method includes:
a. Establishing of a vertical target position for the centering device;
b. Lowering the centering device on the guide arm while monitoring a current vertical position of the centering device until a resistance counteracts further lowering or until the centering device has reached a predefined lowest position;
c. Evaluating the vertical position of the centering device reached in step b),
   i. with a vertical position below the target position signifying that no sample vessel was found,
   ii. with a vertical position that corresponds to this target position signifying that the centering device is centered on a sample vessel, and
   iii. with a vertical position above this target position signifying that the centering device is located on a sample vessel but is not centered.

This method makes it possible to identify automatically whether the sample vessel is present and whether the centering device is centered on the sample vessel. The automatic detection of whether the sample vessel is present and whether the centering is correct increases the reliability of the automation substantially. It is actively checked for this purpose whether a sample vessel is located at the intended position and preparation can be carried out with sample fluid from the sample vessel.

In the prior art, a bar code reader is used for this purpose, or images are created and subjected to a relatively elaborate software-based evaluation. In the case of tightly packed, small sample vessels, however, this is only possible with great effort and expense. An additional gripper module is then necessary, for example, which transports the sample vessel to a barcode reader or which scans the position at which the sample vessel is expected using an additional sensor. This additional effort can be avoided according to the invention.

The contacting of the centering device with the sample vessel can be determined, for example, by monitoring a current through a drive motor for moving the pipetting device vertically. Upon contacting a sample vessel, this current typically rises. The rise in the current can be detected using software. The current vertical position of the centering device can be determined directly using a distance measurement device or indirectly from operating states (e.g., the profile of current consumption over time) of the drive motor.

In case "i.," no sample vessel was found. Then a preparation request will be cancelled. The process continues to the next preparation request. In situation "ii.," everything is ok, and a preparation is processed normally with the sample vessel. In situation "iii.," no centering occurred. This is a critical state that can result in the destruction of the auxiliary cannula and/or pipetting needles or to the loss of the sample. In this case, the preparation is aborted.

The invention further relates to a method for removing sample fluid from a sample vessel using a pipetting device according to the invention, wherein the above-described method according to the invention for detecting a sample vessel is first carried out, and wherein the removal process is aborted in cases i. and iii., and the following additional steps are carried out only in case ii.:
d) Further lowering a top-side suspension of the guide arm against the resilient resistance, so that the auxiliary cannula pierces the septum of the sample vessel;
e) Axially guiding the pipetting needle through the auxiliary cannula into the sample vessel;
f) Aspirating sample fluid from the sample vessel into the pipetting needle;
g) Pulling-out the pipetting needle from the sample vessel;
h) Lifting the top-side suspension of the guide arm until the auxiliary cannula has been pulled out of the septum, the holding-down device pressing against the top side of the sample vessel; and
i) Further lifting the top-side suspension of the guide arm, whereby the centering device detaches from the sample vessel.

The method according to the invention can also be used analogously for dispensing sample fluid into a sample vessel.

This method makes it possible to perform sample preparation in the sample vessel in a reliable and safe manner. Particularly, separate anchoring of the sample vessel on a work platform can be omitted. Through the centering device, it is also ensured that the septum of the sample vessel is pierced in the center. The pipetting needle can thus be reliably protected from damage.

After the auxiliary cannula has pierced into the sample vessel, the thinner pipetting needle is then pushed in, and sample fluid is removed or added. Through a ventilation channel between the auxiliary cannula and the pipetting needle, pressure equalization can occur simultaneously. After the pipetting needle is pulled out, the guide arm also moves upward along with the auxiliary cannula, with the resiliently supported end plate initially remaining with the centering device due to the spring pressure on the sample vessel. After the auxiliary cannula has been pulled completely out of the septum, the guide arm is lifted further, with the end plate being pressed with the centering device by the resilient resistance into a home position that can be defined by a stop on the guide arm. In the home position, a bias of the resilient resistance can remain.

Through the bias, it can be ensured that the centering device is pressed against the sample vessel during the entire process of the auxiliary cannula being pulled out of the septum, with the contact pressure force exceeding the force required for the withdrawal of the auxiliary cannula at all times. The home position of the end plate on the guide arm is preferably reached only after the auxiliary cannula has been pulled completely out of the septum. After the end plate has returned with the centering device into the home position, the centering device also detaches again from the sample vessel.

Additional advantages of the invention follow from the description and the drawing. Likewise, the features cited in the foregoing and in the following can each be utilized according to the invention individually or together in any combination. The embodiments that are shown and described must not be understood as an exhaustive enumeration, but rather as examples intended to illustrate the invention.

BRIEF DESCRIPTION OF THE DRAWINGS

The invention is illustrated in the drawing and is explained in further detail with reference to exemplary embodiments.

DETAILED DESCRIPTION

Figure 1A:
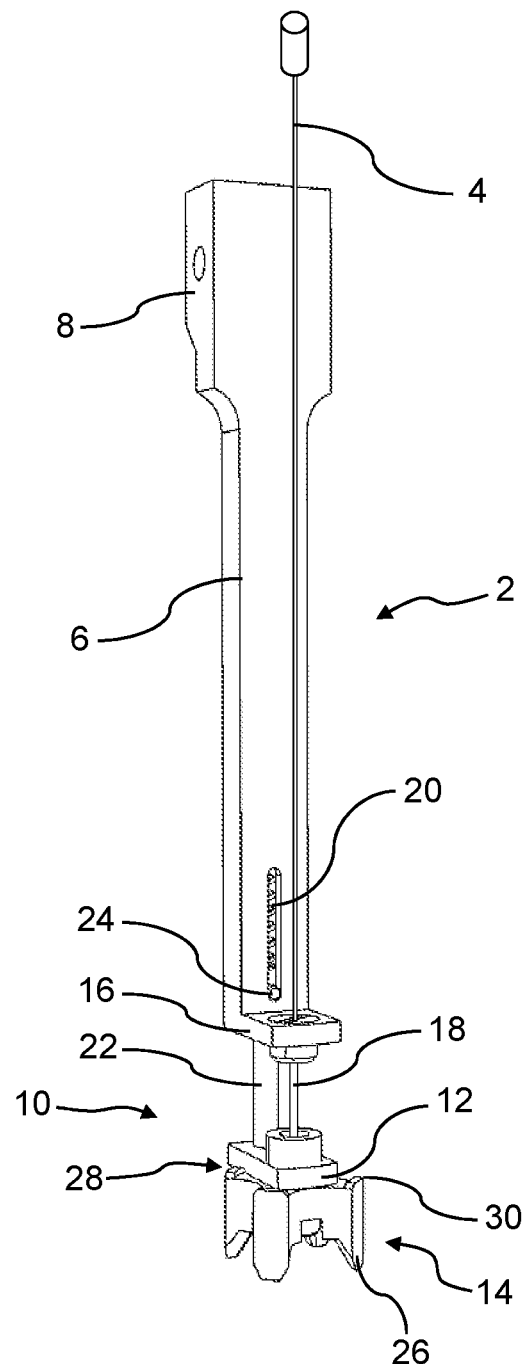
FIG. 1A shows a schematic representation of a pipetting device according to the invention with an end plate in a home position.

FIG. 1A of the drawing shows a schematic view of a preferred embodiment of a pipetting device 2 according to the invention. The pipetting device 2 comprises a pipetting needle 4 and a guide arm 6. The guide arm 6 has a top-side suspension 8. An end plate 12 is arranged at a lower end 10 of the guide arm 6. A centering device 14 is screwed into the end plate 12. A projection 16 is constructed on the guide arm 6 above the end plate 12. An auxiliary cannula 18 is screwed into the projection 16.

The end plate 12 with the centering device 14 can be displaced along the guide arm 6 against a resilient resistance, which is formed here by a spring 20. In order to enable the displaceability, the guide arm 6 has a linear guide 22 with a stop 24. In FIG. 1A, the end plate is in a home position into which it is pushed by the spring 20. Here, the stop 24 defines the home position relative to the upper end 8 of the guide arm 6. In the depicted home position, a free end of the auxiliary cannula 18 is surrounded by the centering device 14.

Here, the centering device 14 has four centering fingers 26 mutually opposing one another in pairs on its bottom side. The centering fingers 26 are distributed here uniformly over the periphery of the centering device 14; that is, all of the centering fingers 26 are spaced at an equal distance from one another. Here, an anti-twist device 28 is constructed on the top side of the centering device 14. Here, the anti-twist device 28 comprises four projections 30. Two of the projections 30 engage laterally around the end plate 12. In this way, it can be ensured that the centering device 14 does not twist with respect to the end plate 12 during the operation of the pipetting device 2. The projections 30 are coordinated here with the end plate 12 such that the centering device 14 can be screwed into the end plate 12 and unscrewed from the end plate 12 without a tool, i.e., with bare hands.

Figure 1B:
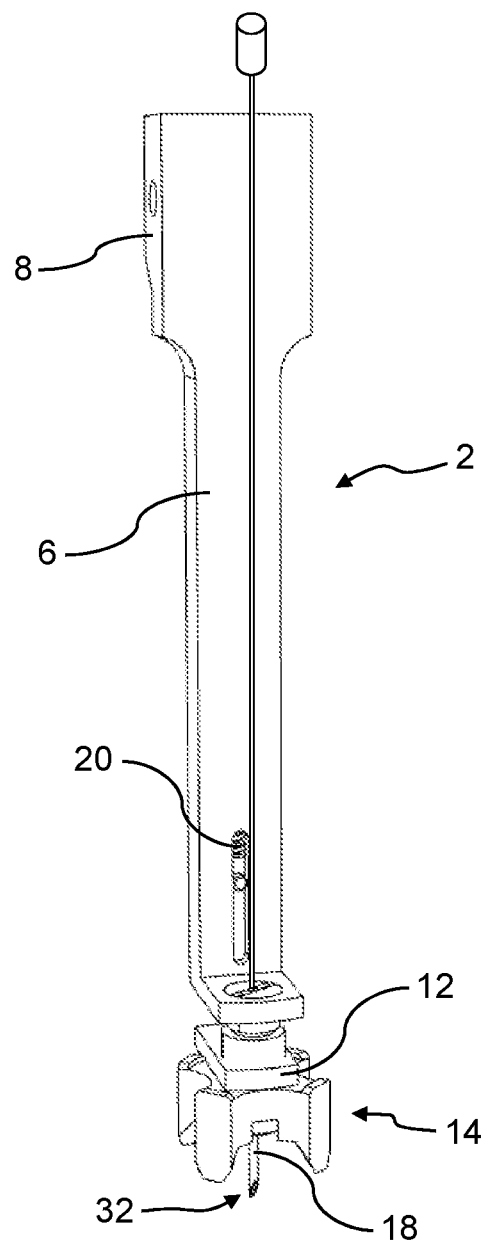
FIG. 1B shows the pipetting device of FIG. 1 with the end plate in a pipetting position.

FIG. 1B shows the pipetting device 2 of FIG. 1A, although here the end plate 12 is displaced upward with the centering device 14 along the guide arm 6 toward the upper suspension 8. The spring 20 has been compressed as a result. The free end 32 of the auxiliary cannula 18 now projects out of the bottom side of the centering device 14.

Figure 2A:
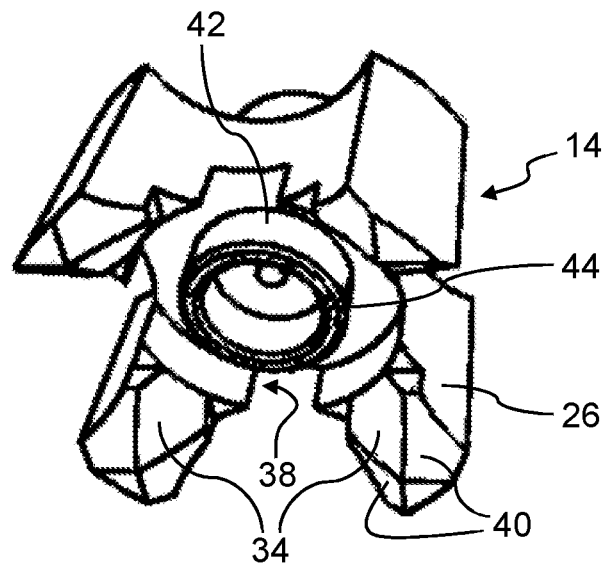
FIG. 2A shows a schematic representation of a centering device for a pipetting device according to the invention in an oblique view from below.

FIG. 2A shows a schematic oblique view from below of a centering device 14 for a pipetting device according to the invention (not shown). Here, the centering device 14 has four uniformly distributed centering fingers 26 mutually opposing one another in pairs. Each centering finger 26 has a conical bevel 34 pointing radially inward. The conical bevels 34 form together a holding-down device for a sample vessel (not shown). A cylindrical-segment-shaped centering recess 38 adjoins the conical bevels 34 of the centering fingers 26 toward the top. The centering fingers 26 are also beveled here on the bottom side in the circumferential direction of the centering device 14 by angled surfaces 40. As a result of the conical bevels 34 and the angled surfaces 40, the centering fingers 26 thus have an overall faceted shape at the bottom end and taper to a point.

Here, the centering device 14 has a lift-off aid 42 on the bottom side between the centering fingers 26 within the centering recess 38. The lift-off aid 42 is designed here in the shape of a cylindrical ring. The lift-off aid 42 also defines an upper stop surface 44 for a sample vessel within the centering recess 38.

Figure 2B:
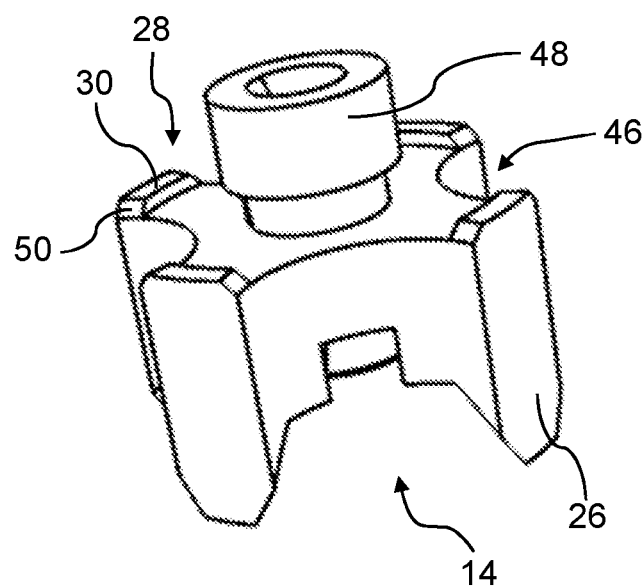
FIG. 2B shows an oblique view from above of the centering device of FIG. 2A.

FIG. 2B shows an oblique top view of the centering device 14 of FIG. 2A. The centering device 14 is designed here with circular-segment-shaped indentations 46 between neighboring centering fingers 26. A threaded portion 48 for engaging in a corresponding thread of an end plate (not shown) is constructed on the top side of the centering device 14. Here, the centering device 14 has a projection 30 above each of the centering fingers 26. The projections 30 form together an anti-twist device 28 for the centering device 14. In the circumferential direction of the centering device 14, each of the projections 30 has two chamfers 50. The chamfers 50 facilitate the locking (snapping-in) of the anti-twist device 28 on an end plate.

Figure 3A:
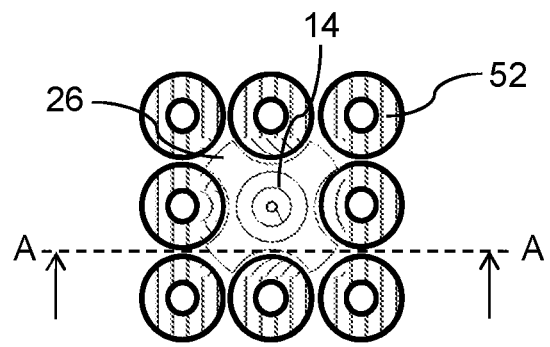
FIG. 3A shows a schematic representation of sample vessels and a centering device for a pipetting device according to the invention in case i. during a method according to the invention.

FIG. 3A shows a schematic view of a centering device 14 of a pipetting device according to the invention (not shown) and eight sample vessels 52 during a method according to the invention.

Figure 3B:
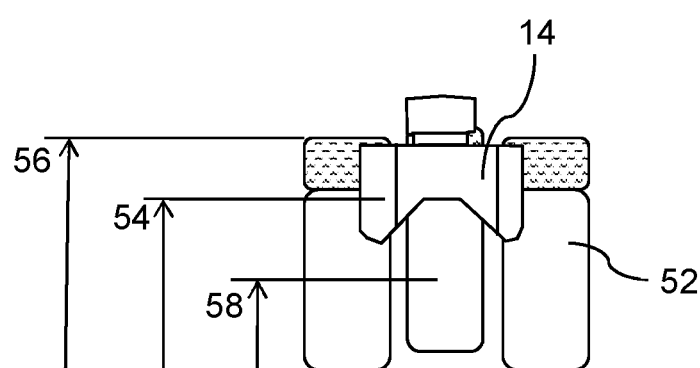
FIG. 3B shows the arrangement of FIG. 3A in a view along sectional line A-A.

FIG. 3B shows the arrangement of FIG. 3A in a side view at sectional plane A-A. Here, the centering device 14 was lowered in the middle between two sample vessels 52. Four centering fingers 26 of the centering device 14 engage in free spaces between the sample vessels 52. Since the middle space for a sample vessel is empty, the centering device 14 was able to be lowered so far that a current vertical position 54 of the centering device 14 lies below a vertical target position 56 for the centering device 14 (case i.). The vertical target position 56 corresponds here to a height of the sample vessels 52. The centering device 14 can be lowered here even farther to a predefined lowest position 58.

Figure 3C:
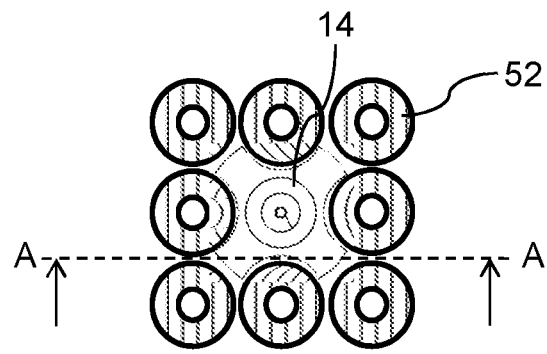
FIG. 3C shows a schematic representation of sample vessels and a centering device for a pipetting device according to the invention in case ii. during a method according to the invention.

FIG. 3C shows a schematic view of a centering device 14 of a pipetting device according to the invention (not shown) and nine sample vessels 52 during a method according to the invention.

Figure 3D:
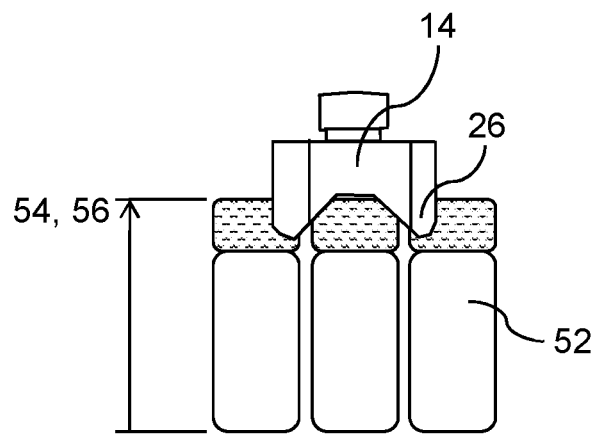
FIG. 3D shows the arrangement of FIG. 3C in a view along sectional line A-A.

FIG. 3D shows the arrangement of FIG. 3C in a side view at sectional plane A-A. Here, a sample vessel 52 is also located in the middle space below the centering device 14 (in FIG. 3C, this sample vessel 52 is covered by the centering device 14). The centering device 14 was therefore able to be lowered just so far that the current vertical position 54 of the centering device 14 corresponds to the vertical target position 56 (case ii.). The sample vessel 52 below the centering device 14 is engaged around by centering fingers 26 of the centering device 14.

Figure 3E:
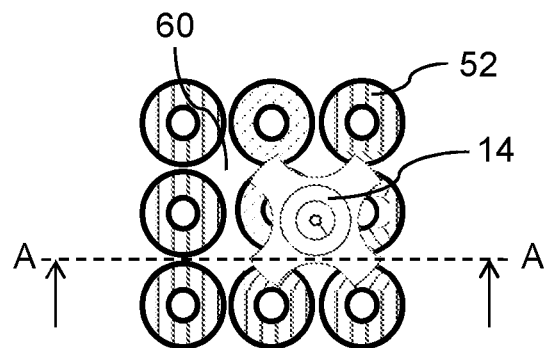
FIG. 3E shows a schematic representation of sample vessels and a centering device for a pipetting device according to the invention in case iii. during a method according to the invention.

FIG. 3E shows a schematic view of a centering device 14 of a pipetting device according to the invention (not shown) and nine sample vessels 52 during a method according to the invention.

Figure 3F:
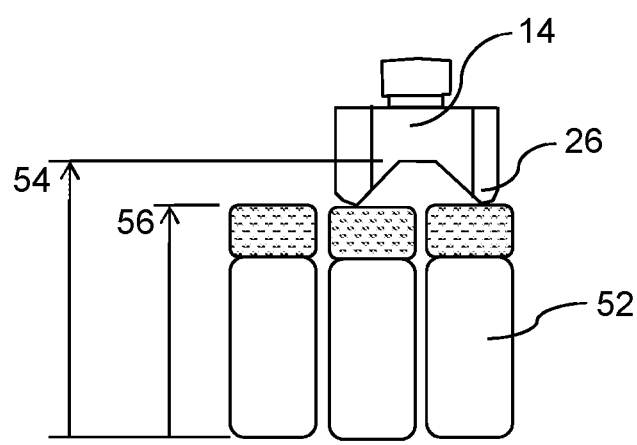
FIG. 3F shows the arrangement of FIG. 3E in a view along sectional line A-A.

FIG. 3F shows the arrangement of FIG. 3E in a side view at sectional plane A-A. Here, the centering device 14 is shifted so far in relation to the middle sample vessel 52 that its centering fingers 26 can no longer engage in free spaces 60 between the sample vessels 52. Instead, the centering fingers 26 rest on the top side of the sample vessels 52. Accordingly, the centering device 14 has remained in a vertical position 54 above the target position 56 (case iii.).

Figure 4A:
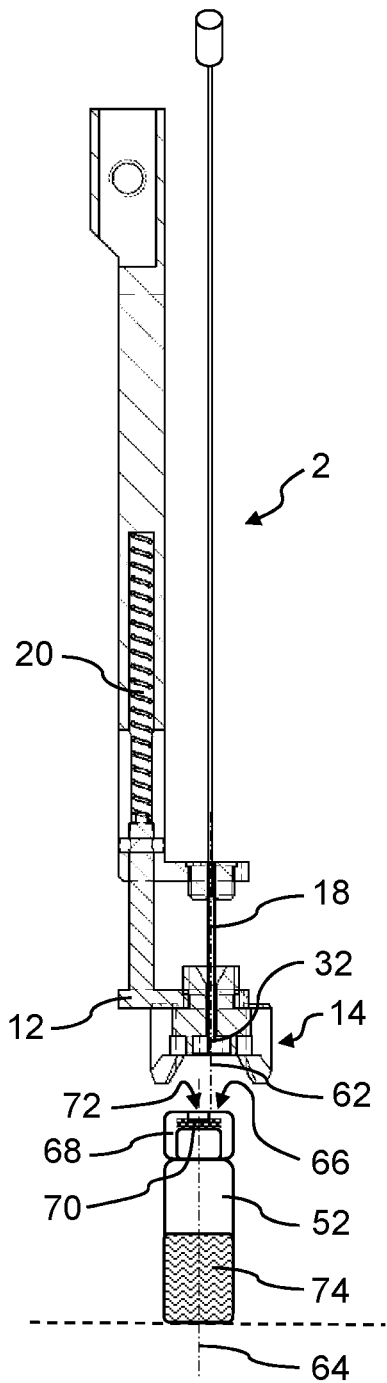
FIG. 4A shows a schematic view of a pipetting device according to the invention above a sample vessel before a pipetting procedure.

FIG. 4A shows a schematic cutaway side view of a pipetting device 2 according to the invention above a sample vessel 52 before a pipetting procedure. An end plate 12 with a centering device 14 is pressed downward by a spring 20 into a home position, so that a free end 32 of an auxiliary cannula 18 is surrounded by the centering device 14. A center axis 62 of the centering device 14 corresponds to a longitudinal axis of the auxiliary cannula 18. Here, the sample vessel 52 is arranged below the centering device 14 such that a vessel axis 64 is offset laterally in relation to the center axis 62. The center axis 62 of the auxiliary cannula 18 points here to a top side 66 of a lid 68 of the sample vessel 52. The lid 68 seals the sample vessel 52 with a septum 70 that is arranged below a central opening 72 in the lid. A sample fluid 74 is located in the sample vessel 52.

Figure 4B:
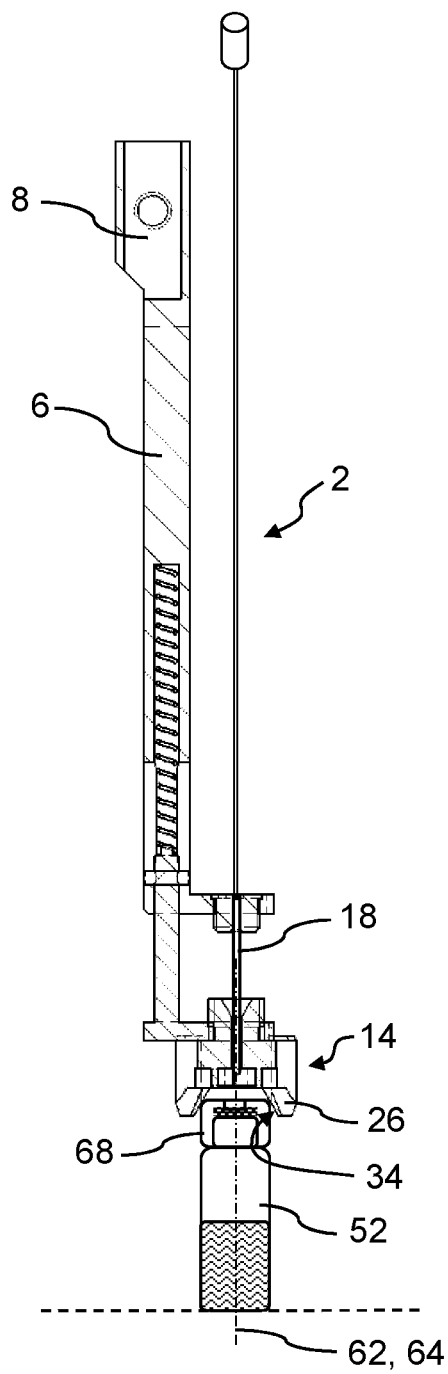
FIG. 4B shows the arrangement of FIG. 4A with centering device placed on the sample vessel.

FIG. 4B shows the pipetting device 2 and the sample vessel 52 of FIG. 4A, but now with the centering device 14 positioned on the sample vessel 52. The centering device 14 was first moved closer to the sample vessel 52 by lowering an upper suspension 8 of a guide arm 6 of the pipetting device 2 until centering fingers 26 of the centering device 14 were able to engage around the sample vessel 52 from the outside. Upon further lowering, the lid 68 of the sample vessel 52 came into contact with the conical bevels 34 of the centering fingers 26. The sample vessel 52 was aligned by the centering device 14 such that the vessel axis 64 now coincides with the center axis 62 of the centering device 14 and the identical longitudinal axis of the auxiliary cannula 18.

Figure 4C:
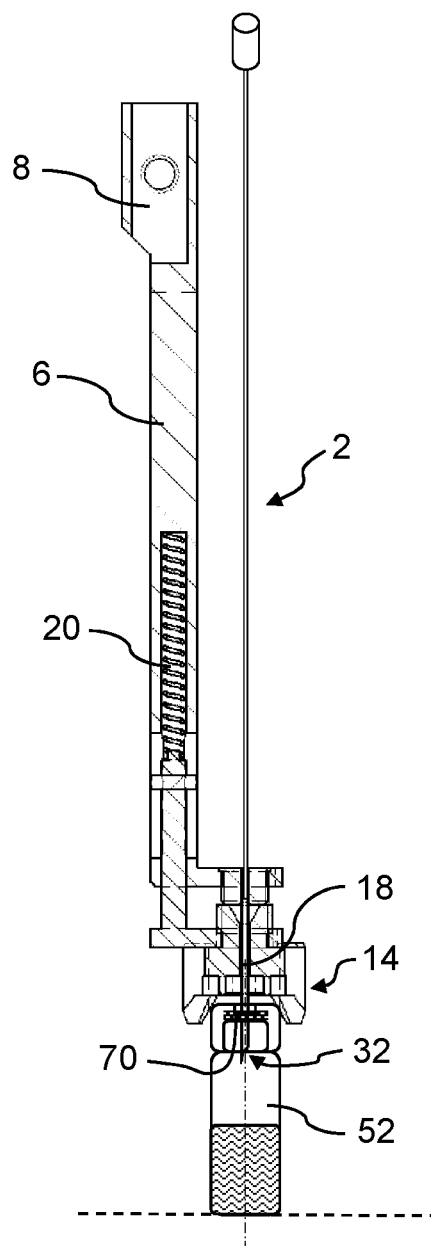
FIG. 4C shows the arrangement of FIG. 4A with auxiliary cannula inserted into the septum of the sample vessel.

FIG. 4C shows the pipetting device 2 of FIG. 4A, 4B, but with the upper suspension 8 of the guide arm 6 having been lowered even farther compared to the state in FIG. 4B. The free end 32 of the auxiliary cannula 18 has thus pierced the septum 70 of the sample vessel 52. The centering device 14 is pressed by the compressed spring 20 onto the sample vessel 52. The centering device 14 has the effect that the auxiliary cannula 18 has pierced the septum 70 precisely in the center.

Figure 4D:
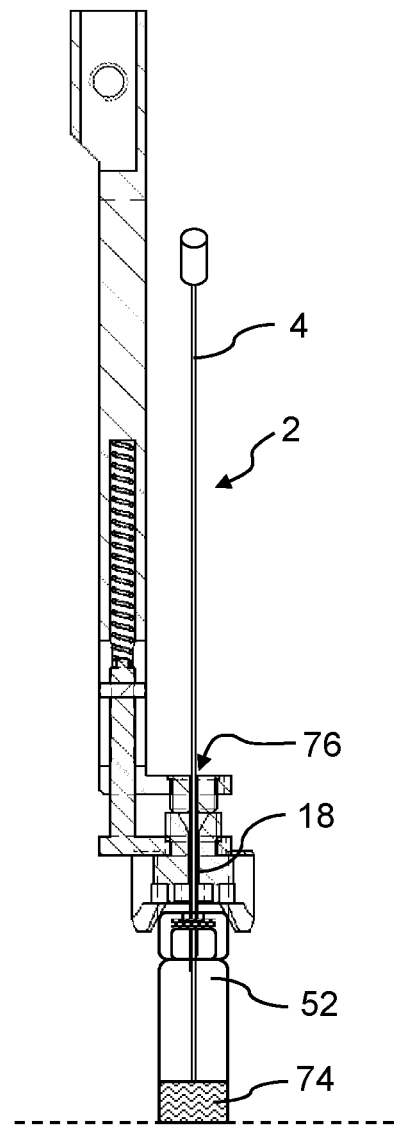
FIG. 4D shows the arrangement of FIG. 4A with pipetting needle introduced into the sample vessel.

FIG. 4D shows the pipetting device 2 of FIGS. 4A-4C, but unlike in FIG. 4C, a pipetting needle 4 has now been inserted into the sample vessel 52. The pipetting needle 4 was guided axially through the auxiliary cannula 18 for this purpose. A ventilation channel 76 is constructed between the pipetting needle 4 and the auxiliary cannula 18 by an outer surface of the pipetting needle 4 being spaced apart from an inner surface of the auxiliary cannula 18. To achieve this, an outside diameter of the pipetting needle 4 is about 10% less than an inside diameter of the auxiliary cannula 18. The pipetting needle 4 was advanced so far that it has dipped into the sample fluid 74. Sample fluid 74 was then aspirated into the pipetting needle 4.

Figures 4E, 4F:
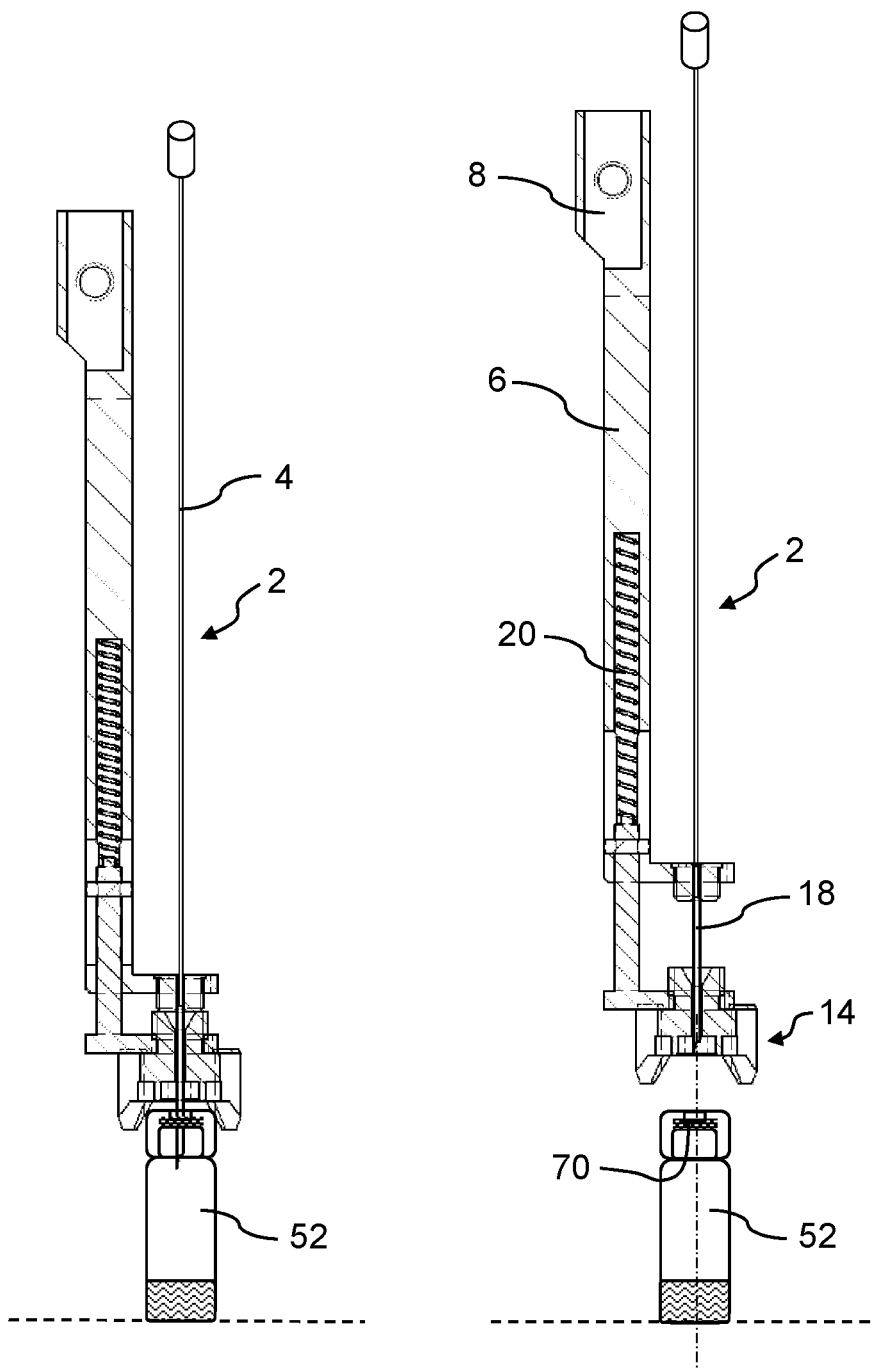
FIG. 4E shows the arrangement of FIG. 4A with pipetting needle pulled out of the sample vessel.
FIG. 4F shows the arrangement of FIG. 4A with pipetting device lifted from the sample vessel after conclusion of the pipetting procedure.

FIG. 4E shows the pipetting device 2 of FIGS. 4A-4D, but unlike in FIG. 4D, the pipetting needle 4 with suctioned sample fluid has been pulled upward out of the sample vessel 52.

FIG. 4F shows the pipetting device 2 of FIGS. 4A-4E, but the auxiliary cannula 18 has now been pulled out of the septum 70 and the centering device 14 has been lifted from the sample vessel 52. Upon lifting of the upper suspension 8 of the guide arm 6, the auxiliary cannula 18 was first pulled out of the septum 70. Meanwhile, the centering device 14 was also pressed by the spring 20 against the sample vessel 52. After the centering device 14 had reached its home position relative to the upper suspension 8, the centering device 14 was also removed upward from the sample vessel 52 as the upper suspension 8 continued to be lifted. The pipetting procedure is thus concluded.

Figure 5A:
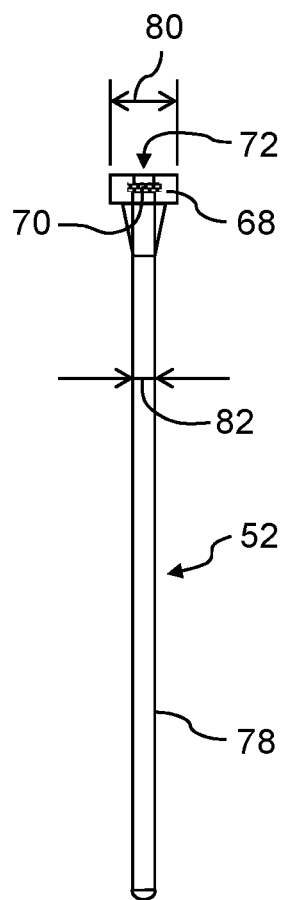
FIG. 5A shows a first embodiment of a very thin sample vessel for a pipetting device according to the invention.

FIG. 5A shows a first embodiment of a very thin sample vessel 52 for a pipetting device according to the invention (not shown). The sample vessel 52 is embodied here as a first NMR tube (NMR sample vessel) with an outside diameter of greater than 2.5 mm and a length of greater than 150 mm. The sample vessel 52 comprises a substantially hollow-cylindrical body 78 and a lid 68. A central opening 72 is constructed in the lid 68 and is sealed by a septum 70. An outside diameter 80 of the lid 68 is about 8 mm here. An inside diameter 82 of the body 78 corresponds to an opening diameter of the opening 72 and is about 2.5 mm here.

Figure 5B:
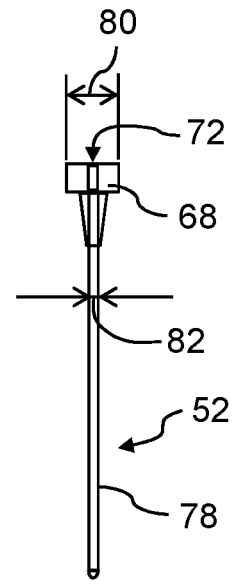
FIG. 5B shows a second embodiment of a very thin sample vessel for a pipetting device according to the invention.

FIG. 5B shows a second embodiment of a very thin sample vessel 52 for a pipetting device according to the invention (not shown). The sample vessel 52 is embodied here as a second NMR tube (NMR sample vessel) with an outside diameter of less than 2.5 mm and a length of less than 150 mm. The second embodiment of the sample vessel 52 of FIG. 5B corresponds in its basic structure to the first embodiment of FIG. 5A. However, an outside diameter 80 of the lid 68 is only about 6 mm here. An inside diameter 82 of a substantially hollow-cylindrical body 78 corresponds here to an opening diameter of a central opening 72 in the lid 68 and is about 1.0 mm here.

Figure 6A:
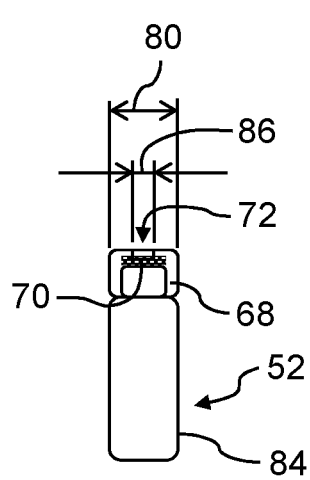
FIG. 6A shows a third embodiment of a sample vessel for use with a pipetting device according to the invention.

FIG. 6A shows a third embodiment of a sample vessel 52 for a pipetting device according to the invention (not shown). Here, the sample vessel 52 is embodied as an auto-sampler vial. The sample vessel 52 comprises a vial body 84 and a lid 68. A central opening 72 is constructed in the lid 68 and is sealed by a septum 70. An outside diameter 80 of the lid 68 is about 11 mm here. An opening diameter 86 of the central opening 72 in the lid 68 is about 3 mm here.

Figure 6B:
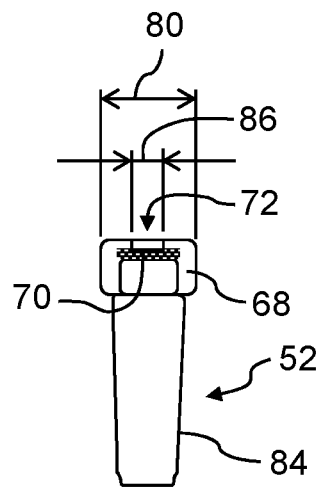
FIG. 6B shows a fourth embodiment of a sample vessel for use with a pipetting device according to the invention.

FIG. 6B shows a fourth embodiment of a sample vessel 52 for a pipetting device according to the invention (not shown). Here, the sample vessel 52 is embodied as a cryo-vial. The sample vessel 52 comprises a vial body 84 and a lid 68. The vial body 84 is conical (tapering toward the bottom). A central opening 72 is constructed in the lid 68 and is sealed by a septum 70. An outside diameter 80 of the lid 68 is about 14 mm here. An opening diameter 86 of the central opening 72 in the lid 68 is about 4 mm here.

Figure 7:
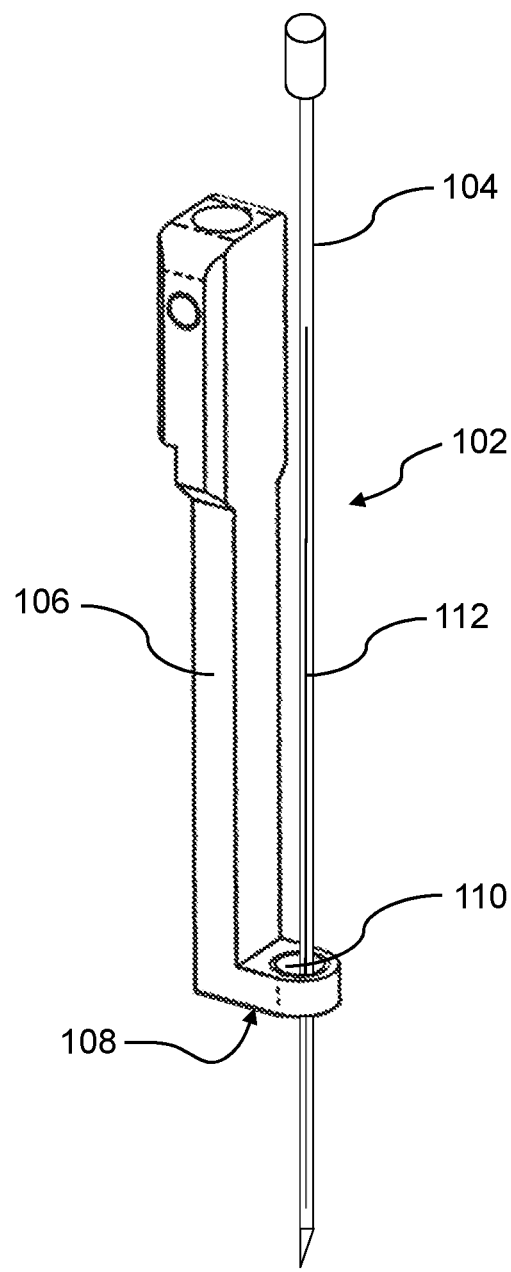
FIG. 7 shows a pipetting device with a freely hanging septum-piercing needle from the prior art.

FIG. 7 shows a pipetting device 102 with a freely hanging septum-piercing needle 104 from the prior art. In this pipetting device 102 from the prior art, the septum piercing needle 104 is used both to pierce a septum of a sample vessel (not shown) and for aspirating sample fluid from the sample vessel. Besides the septum piercing needle 104, the pipetting device 102 comprises a guide arm 106. A holding-down device 108 is constructed on the bottom side of the guide arm 106. The septum piercing needle 104 projects through a recess 110 that is constructed on the holding-down device 108, without being guided or supported in the recess 110. A longitudinal engraving 112 on the outside of the septum piercing needle 104 serves to ventilate the sample vessel when the septum piercing needle 104 has pierced the septum of the sample vessel.

What is claimed is:

1. A pipetting device for removing sample fluid from a sample vessel that is sealed on a top side with a septum, comprising:
   a pipetting needle and an auxiliary cannula configured to pierce the septum and to guide the pipetting needle axially through the auxiliary cannula,
   a guide arm on the lower end of which is arranged an end plate configured to axially displace along the guide arm against a resilient resistance,
   a centering device configured to insert into the end plate of the guide arm and having a radial outside surface disposed around a circumference on the centering device, and
   at least three centering fingers with conical bevels constructed on the radial outside of the centering device, distributed around the circumference of the centering device, forming a holding-down device for the sample vessel, and configured to engage around the top side of the sample vessel and from outside the sample vessel.

2. The pipetting device according to claim 1, wherein the centering device is configured to screw into the end plate.

3. The pipetting device according to claim 1, wherein the centering device is configured to snap into, clamp into, or insert, via a bayonet socket, into the end plate.

4. The pipetting device according to claim 1, further comprising an anti-twist device configured to enable a defined alignment of the centering device relative to the end plate, wherein the anti-twist device comprises at least two top-side projections on the centering device that engage laterally around the end plate.

5. The pipetting device according to claim 4, wherein the anti-twist device comprises four of the top-side projections.

6. The pipetting device according to claim 1, wherein the centering device has a bottom side from which a lift-off aid extends coaxially to the auxiliary cannula.

7. The pipetting device according to claim 6, wherein the lift-off aid has an annular shape.

8. The pipetting device according to claim 1, further comprising a ventilation channel for the sample vessel between the auxiliary cannula and the pipetting needle when the pipetting needle is located to pass axially through the auxiliary cannula.

9. The pipetting device according to claim 1, wherein the centering fingers of the centering device are beveled on a bottom side around the circumference of the centering device.

10. The pipetting device according to claim 1, wherein the centering device has circular-segment-shaped indentations between the centering fingers.

11. The pipetting device according to claim 1, wherein the centering fingers are distributed at regular intervals along a periphery of the centering device.

12. The pipetting device according to claim 1, wherein the centering device comprises four centering fingers arranged in opposing pairs.

13. The pipetting device according to claim 1, wherein the centering device is further configured to insert into the end plate of the guide arm and to retract from the end plate.

14. A method for detecting a sample vessel with a pipetting device as claimed in claim 1, comprising:
   a. establishing an axial target position for the centering device;

b. axially displacing the centering device along the guide arm while monitoring a current axial position of the centering device until a resistance counteracts further lowering or until the centering device has reached a predefined axially lowest position;
c. evaluating the vertical position of the centering device reached in said step b),
    i. wherein an axial position below the target position corresponds to a failure to detect a presence of a sample vessel,
    ii. an axial position at least approximately at the target position corresponds to detection of the centering device centered on a sample vessel, and
    iii. an axial position axially above the target position corresponds to detection of the centering device located on but not centered on a sample vessel.

15. A method for removing sample fluid from a sample vessel using a pipetting device, comprising:
    performing the method for detecting the sample vessel as claimed in claim 14, and in the event of the evaluation outcome (i) or the evaluation outcome (iii), aborting the removal process, and
    in the event of the evaluation outcome (ii):
    d. further axially displacing a top-side suspension of the guide arm against the resilient resistance, such that the auxiliary cannula pierces the septum of the sample vessel;
    e. axially guiding the pipetting needle through the auxiliary cannula into the sample vessel;
    f. aspirating sample fluid out of the sample vessel and into the pipetting needle;
    g. retracting the pipetting needle from the sample vessel;
    h. lifting the top-side suspension of the guide arm until the auxiliary cannula has been retracted out of the septum and while the holding-down device presses against the top side of the sample vessel; and
    i. further lifting the top-side suspension of the guide arm, whereby the centering device detaches from the sample vessel.

* * * * *